(12) United States Patent
Leathers et al.

(10) Patent No.: US 9,326,703 B2
(45) Date of Patent: May 3, 2016

(54) THERAPEUTIC MANIPULATION DEVICE

(75) Inventors: Kevin P. Leathers, Kirkland, WA (US);
Chris Doughty, Kirkland, WA (US);
Phillip Horvath, Kirkland, WA (US)

(73) Assignee: ORTHO-NEURO TECHNOLOGIES, INC., Kirkland, WA (US)

( * ) Notice: Subject to any disclaimer, the term of this patent is extended or adjusted under 35 U.S.C. 154(b) by 1415 days.

(21) Appl. No.: 13/045,004

(22) Filed: Mar. 10, 2011

(65) Prior Publication Data

US 2011/0224580 A1 Sep. 15, 2011

Related U.S. Application Data

(60) Provisional application No. 61/313,070, filed on Mar. 11, 2010.

(51) Int. Cl.
*A61B 5/103* (2006.01)
*A61H 1/00* (2006.01)
*G09B 23/28* (2006.01)
*A61B 5/00* (2006.01)

(52) U.S. Cl.
CPC .............. *A61B 5/103* (2013.01); *A61B 5/4836* (2013.01); *A61H 1/008* (2013.01); *G09B 23/28* (2013.01); *A61B 5/4528* (2013.01); *A61B 2562/0233* (2013.01); *A61H 2201/5061* (2013.01); *A61H 2201/5069* (2013.01); *A61H 2201/5079* (2013.01)

(58) Field of Classification Search
CPC ...................................................... A61H 39/00
USPC .......................................... 434/262, 275, 265
See application file for complete search history.

(56) References Cited

U.S. PATENT DOCUMENTS

| 1,001,530 A | 8/1911 | Kaesen |
| 4,159,640 A | 7/1979 | Leveque et al. |
| 4,554,910 A | 11/1985 | Lally |

(Continued)

FOREIGN PATENT DOCUMENTS

| WO | WO99/40880 | 8/1999 |
| WO | 2009/031803 A1 | 3/2009 |
| WO | 2009/105564 A2 | 8/2009 |

OTHER PUBLICATIONS

Stolowitz Ford Cowger Listing of Related Cases, May 30, 2011.

(Continued)

*Primary Examiner* — Bruk Gebremichael
(74) *Attorney, Agent, or Firm* — Schwabe, Williamson & Wyatt (57) ABSTRACT

A manipulation device is programmable with different parameters associated with different manipulation exercises for different types of simulated patients. A measuring system determines the success or failure for any of the programmable manipulation exercises and tracks specific results that precisely track how close a student comes to specific target force values. This allows a student to more accurately track performance improvements and more effectively focus practice sessions on problem manipulation techniques. The measurement system not only measures the time and force values associated with the manipulation exercises but also measures angular displacement of the manipulation apparatus during the manipulation exercise. This allows the student to not only determine if a proper amount of force was applied during the manipulation exercise but also to determine if the force was maintained in the same direction and angle.

7 Claims, 9 Drawing Sheets

(56) References Cited

U.S. PATENT DOCUMENTS

| | | |
|---|---|---|
| 5,158,096 A | 10/1992 | Clark et al. |
| 5,239,988 A | 8/1993 | Swanson et al. |
| 5,392,649 A | 2/1995 | Yoo |
| 5,487,722 A | 1/1996 | Weaver, II et al. |
| 5,496,257 A | 3/1996 | Kelly |
| 5,582,580 A | 12/1996 | Buckman, Jr. et al. |
| 5,589,639 A | 12/1996 | D'Antonio et al. |
| 5,645,522 A | 7/1997 | Lurie et al. |
| 6,013,041 A | 1/2000 | Leathers |
| 6,068,596 A | 5/2000 | Weth et al. |
| 2004/0134274 A1* | 7/2004 | Hoggan et al. ............. 73/379.01 |
| 2006/0009719 A1 | 1/2006 | Lajoie |
| 2007/0038166 A1 | 2/2007 | Ulrich |
| 2009/0054814 A1* | 2/2009 | Schnapp et al. ............. 600/595 |

OTHER PUBLICATIONS

International Search Report for PCT/US11/027919; Date of Mailing Apr. 12, 2012.

International Search Report for PCT/US99/002826; Date of Mailing Apr. 15, 1999.

* cited by examiner

FIG. 7

THERAPEUTIC MANIPULATION DEVICE

The present application claims priority to U.S. Provisional No. 61/313,070 filed Mar. 11, 2010 which is herein incorporated by reference. The present application incorporates by reference U.S. Pat. No. 6,013,041 in its entirety.

BACKGROUND OF THE INVENTION

Therapeutic manipulation is utilized by therapists, such as chiropractors, osteopathic physicians, physiatrists and, in some cases, physical therapists, to realign the joints of a patient's spine. Manipulation involves the therapist applying pre-manipulative tension prior to administering an impulse to a patient's joint along a predetermined vector.

Figure 1:
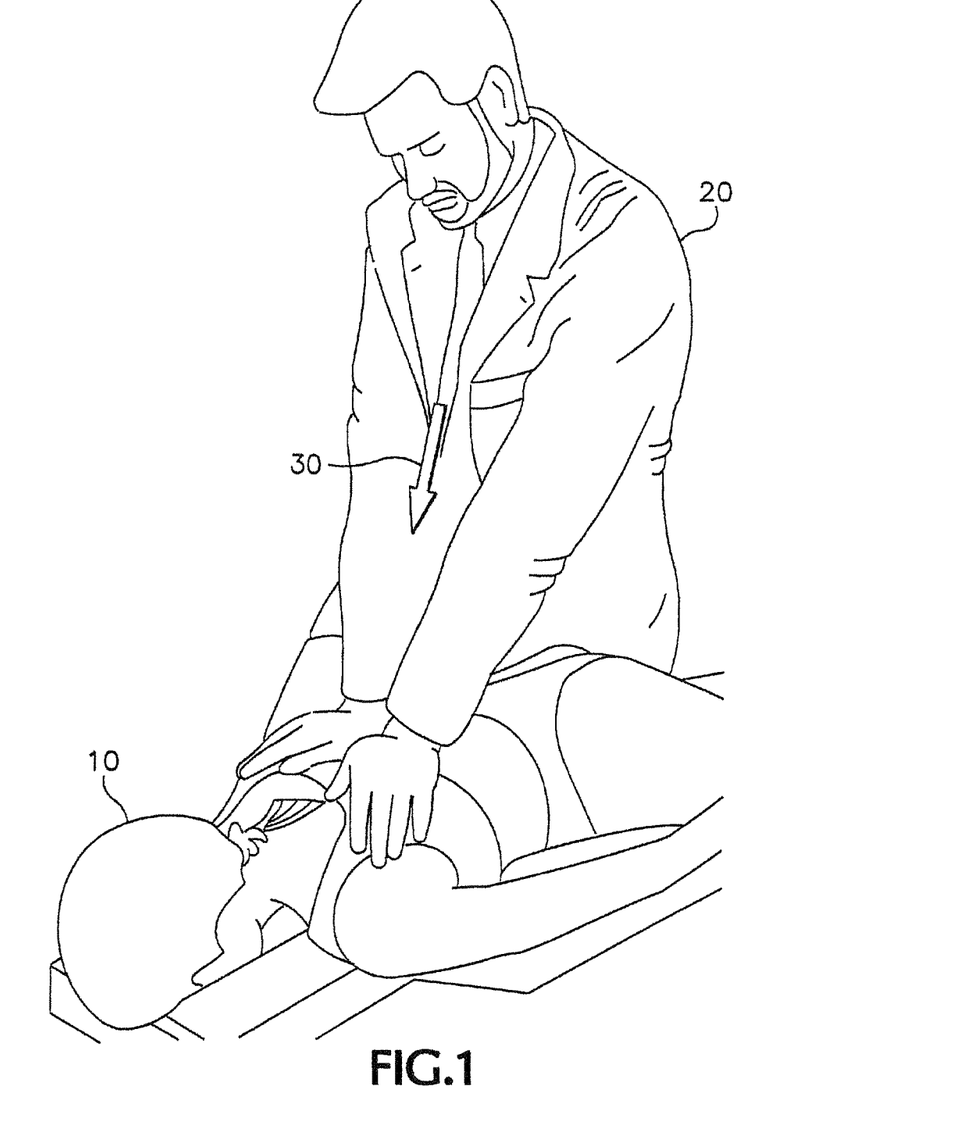
FIG. 1 illustrates a therapeutic manipulation being performed on a patient.

FIG. 1 illustrates one example of a prior art therapeutic manipulation being administered by a therapist 20 to a patient 10. A vector 30 represents the thrust force of the therapeutic manipulation. Therapeutic manipulations are performed in any region of the spine and in a variety of doctor to patient positions.

The safety, comfort and effectiveness of a manipulative impulse or thrust is improved if the impulse is delivered with a high degree of speed along the plane of the joint under manipulation. However, an impulse that is delivered with too great of an amplitude can injure the patient. Therapists practice manipulations in order to develop the psychomotor skills necessary to deliver high speed, controlled amplitude impulses along a given plane. One practice technique is to deliver impulses into inanimate objects. However, delivering impulses to inanimate objects risk injury to the shoulders or wrists of the therapist. Another training technique is to deliver impulses to a training partner, which risks injury to the training partner from high-amplitude impulses. In addition, for both these practice techniques, it is difficult to accurately measure the force and speed of the practice impulses.

SUMMARY OF THE INVENTION

A therapeutic manipulation device includes an elongate housing having an axial cavity and a reciprocating member that inserts into the cavity. The manipulation device is programmable with different parameters associated with different manipulation exercises and different types of simulated patients. A measuring system determines the success or failure for any of these programmable manipulation exercises and tracks specific results that precisely track how close a student came to specific target force values. This allows a student to more accurately track performance improvement and more effectively focus practice sessions on problem manipulation techniques. The measurement system not only measures the time and force values associated with the manipulation exercises but also measures angular displacement of the practice apparatus during the manipulation exercise. This allows the student to not only determine if a proper amount of thrust force was applied during the manipulation exercise but also determine if the force was maintained in the right direction and angle.

The foregoing and other objects, features and advantages will become more readily apparent from the following detailed description of a preferred embodiment which proceeds with reference to the accompanying drawings.

DETAILED DESCRIPTION

A spinal manipulation simulating device allows students to develop the psychomotor skills necessary to deliver high speed, controlled amplitude impulses along a given plane. The device aids in the strength and speed training of the specific muscle groups of the student used for delivering therapeutic manipulations by presenting resistance during a simulated manipulation.

Figure 2:
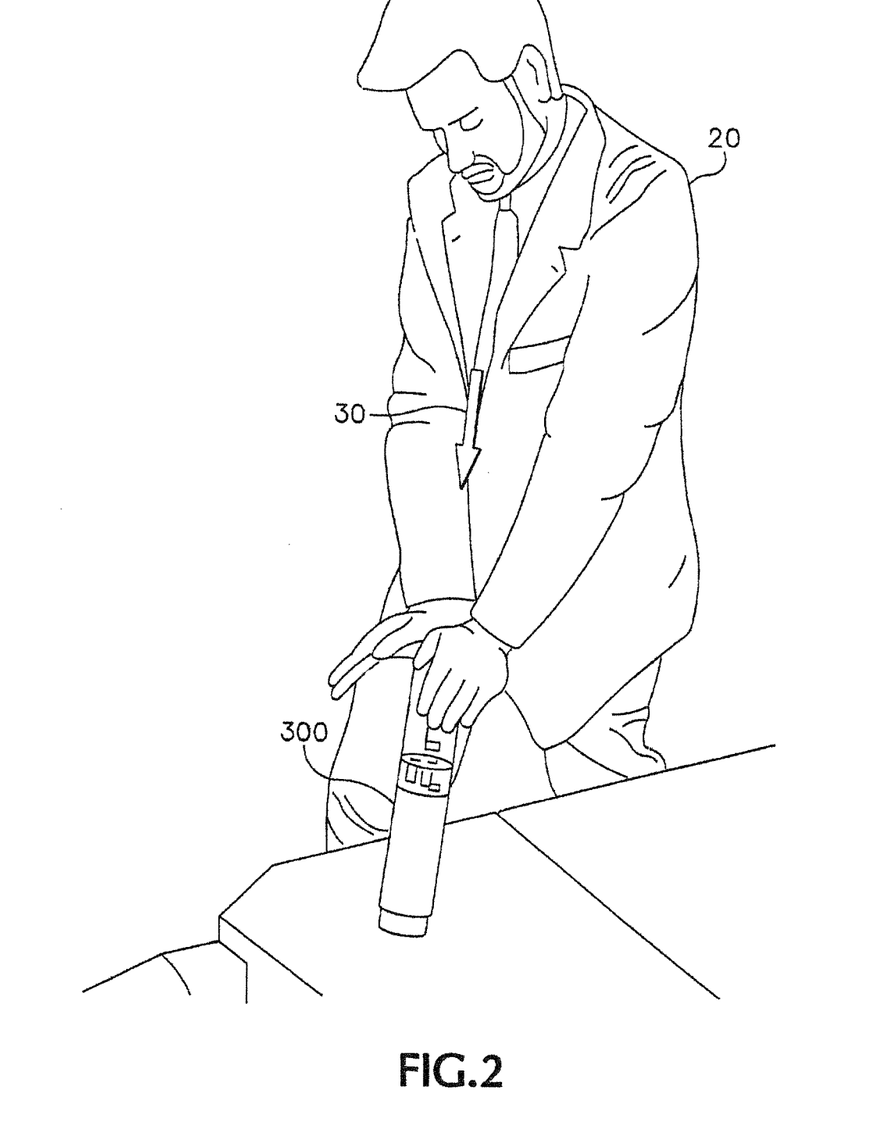
FIG. 2 illustrates a manipulation device being used for practicing and monitoring the therapeutic manipulation of FIG. 1.

FIG. 2 illustrates a therapist 20 performing the therapeutic manipulation of FIG. 1 with an embodiment of the apparatus 300. An impulse is delivered to the apparatus 300 with the force vector 30. The apparatus 300 can also be utilized to simulate other doctor to patient positions corresponding to a variety of spinal manipulations.

Figure 3:
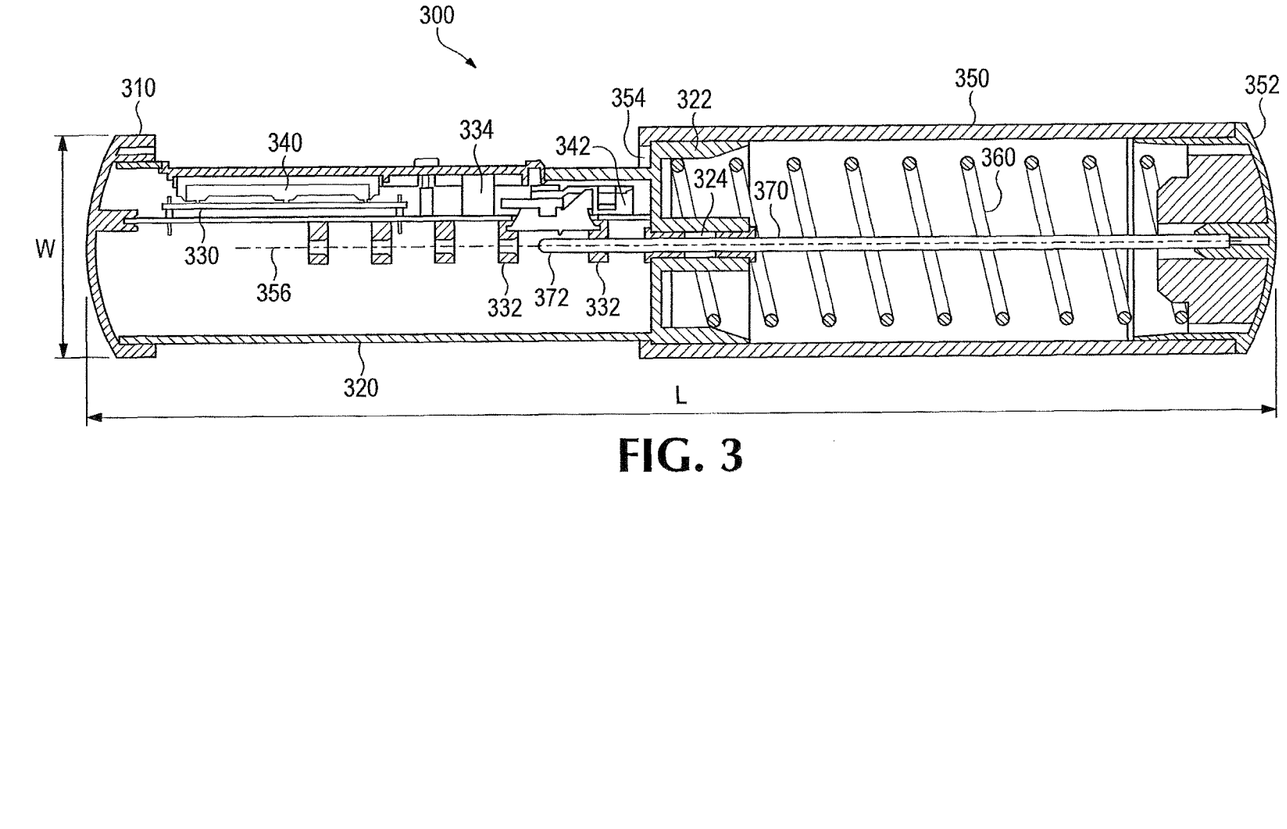
FIG. 3 is a side cut-away view of the manipulation device shown in FIG. 2.

A sectional side view of apparatus 300 is illustrated in FIG. 3. The apparatus 300 includes an elongate housing 350 having a closed end 352 and an open axial cavity 354 opposite closed end 352. An elongate reciprocating body 320 has one end enclosed by cap 310 and another end 322 which includes an aperture 324 to accommodate a displacement member 370. The elongate reciprocating body 320 is sized to fit inside elongate housing 350 and slide freely along a lengthwise axis 356 of elongate housing 350. Elongate reciprocating body 320 and elongate housing 350 are cylindrical in shape but can be constructed to be non-cylindrical as long as the cavity 354 formed by elongate housing 350 permits insertion and reciprocating motion of elongate reciprocating body 320.

The width W of the apparatus 300 is selected to approximate the size of a motion segment of the thoracic or lumbar spine. A motion segment is typically two adjacent vertebrae. The length L of apparatus 300 is selected to approximate the depth of an average person lying supine with his arms across his chest, which is a typical position for supine thoracic manipulation. The length L also approximates the width of a patient's hips in order to allow simulation of lumbar manipulations with the patient in a side posture position. The cylindrical shape and reciprocating nature of the reciprocating body 320 and elongate housing 350 serve to encourage focus of the therapist's line of drive along a single plane and axis which can be selected by the therapist to correspond to a plane and angle of a spinal joint under simulation. The apparatus 300 can also be incorporated into a human dummy in order to simulate manipulations using a more lifelike simulation tool.

A biasing member 360 also fits within elongate housing 350 between closed end 352 of elongate housing 350 and end 322 of elongate reciprocating body 320. Biasing member 360 in one embodiment is a coiled spring and biases elongate reciprocating body 320 to a position within the axial cavity of elongate housing 350 where the combined length of elongate reciprocating body 320 and elongate housing 350 is approximately fourteen inches. Biasing member 360 generates an elastic resistance force along axis 356 which resists the further insertion of reciprocating body 320 into elongate housing 350.

Figure 5:
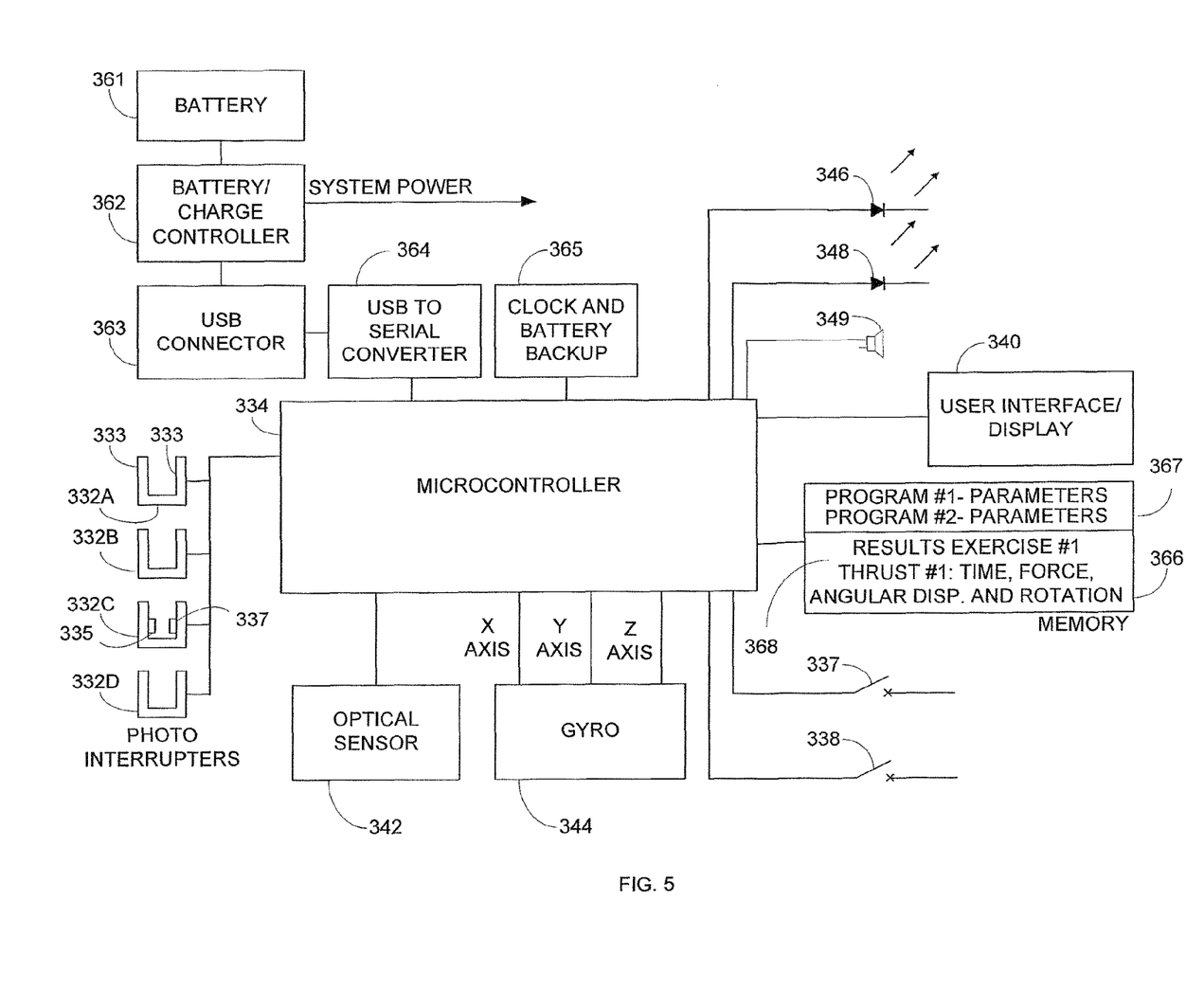
FIG. 5 is a block diagram of a control system used in the manipulation device of FIG. 3.

Other devices, such as a sealed gas envelope, can also be used as biasing member 360. The biasing member 360 can be replaced with springs of different stiffness to increase or reduce the resistance as the therapist's strength varies with practice. In another embodiment, a piston and air cylinder configuration can be used. In this embodiment, the housing 350 contains an air cylinder that can be pumped up via an air valve. A transducer is located inside of the air cylinder and determines an internal air pressure. The transducer sends a signal to a microcontroller 334 (FIG. 5). The microcontroller adjusts the reference points used during manipulation exercises according to the detected air pressure in the air cylinder.

In the embodiment in FIG. 3, the displacement member 370 is a reciprocating rod attached to the closed end 352 and disposed along axis 356 of elongate housing 350 through the aperture 324 in end 322 of reciprocating body 320. As reciprocating body 320 is pushed into the axial cavity 354 of elongate housing 350, tip 372 of rod 370 extends farther into reciprocating body 320 along axis 356. A circuit board 330 retains a user interface and display 340 and a processor 334 (CPU) within elongate reciprocating body 320.

Figure 4:
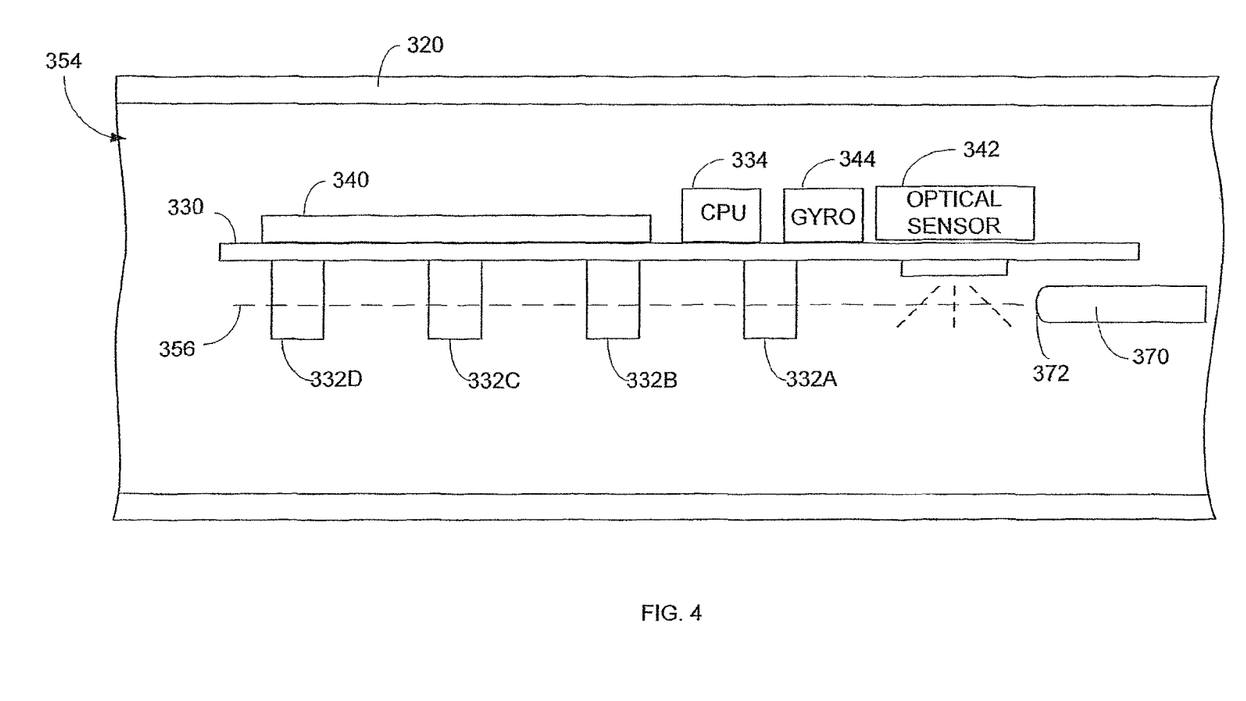
FIG. 4 illustrates a portion of the manipulation device of FIG. 3 in more detail.

FIG. 4 is an isolated side view of the device shown in FIG. 3 illustrating in more detail the circuit board 330 disposed within reciprocating body 320. Circuit board 330 includes sensors 332 and 342 disposed along axis 356 and connected to the processor 334 to form a measuring system for measuring the displacement of reciprocating body 320 relative to elongate housing 350. Light gates such as photo interrupters 332 sense the passage of tip 372 (FIG. 3) of rod 370. The sensor in one embodiment is an optical sensor 342 similar to the type used in computer mice and detects a relative movement in the rod 370. The optical sensor 342 captures an image of a textured surface of the rod 370 and then detects any changes or movement in the captured image.

In one embodiment, the displacement member 370 is a steel rod that slides parallel to the surface of circuit board 330. The rod 370 passes over the optical sensor 342. The optical sensor 342 provides data regarding relative changes in rod position and passes that information to the microcontroller 334. The photo interrupters 332 provide a logic level signal to the microcontroller 334 when the rod 370 blocks or breaks the optical path between two opposite legs 333 shown in FIG. 5. A multitude of the photo interrupters 332 provide a number of reference points along the distance traveled by the rod 370.

The combination of optical sensor 342 and photo interrupters 332 provide an absolute position reference for any displacement of the rod 370. Combined, the optical sensor 342 gives a displacement resolution of around 400 counts per inch and the photo interrupters 332 provide an absolute position reference. This allows the processor/CPU 334 to provide very precise and reliable measurements of the force applied to the apparatus 300. Thus, the processor 334 can not only determine if the applied force applied to apparatus 300 was within some acceptable range, but can also identify the precise difference between the applied force and any programmable reference value. This allows students to more accurately monitor their progress since the processor 334 indicates precisely how close an applied force or thrust comes to a particular target parameter.

A gyroscope 344 is used by the processor 334 to identify angular displacements in the applied force. For example, a student may apply the correct amount force, but might apply the force in the wrong direction or may vary the angle of the applied force. In other words, the thrust may not be maintained along the correct axis. The student may also apply a rotational torque when applying the force. For example, the student may twist their hand when applying a force to apparatus 300. This angular displacement and torque may or may not be desirable, depending on the particular therapeutic manipulation that is currently being performed. The gyroscope 344 measures the angular rate of thrust along an X-axis, Y-axis, and Z-axis. The measurements along the X and Z axes are used for identifying any changes in the angular displacement of the apparatus 300 during a thrust. The measurements in the Y-axis are used for identifying the angular rotation or torque applied to the apparatus during the thrust. These measurements will be described in more detail below in FIGS. 8 and 9.

FIG. 5 is a circuit diagram that shows the electrical components coupled to the circuit board 330. The processor 334 is alternatively referred to as a microcontroller 334 or a Central Processing Unit (CPU) and can be any type of logic device that monitors manipulation exercises. The photo interrupters 332A-332D as described above provide reference points for the position measurements of rod 370. The photo interrupters 332 each include two legs 333 that extend up along opposite sides of the rod 370. One of the legs 333 includes a light transmitter 335 and the other leg includes a light sensor 337. The rod 370 when inserted in between the two legs 333 blocks an optical beam transmitted between the two legs 333. In response to the blocked beam, a signal is sent back to the processor 334 indicating the rod 370 has reached a particular reference location associated with the physical location of that particular photo interrupter 332A-332D.

As also described above, the optical sensor 342 generates a signal used by the processor 334 to identify the incremental movements of the rod 370 in-between adjacent photo interrupters 332. The gyroscope 344 generates signals identifying changes in the position of apparatus 300 in the X, Y, and Z axis. The processor 344 uses the signals generated by gyroscope 344 to identify changes in the angular displacement and angular rotation of the apparatus 300 during a manipulation exercise.

A clock and battery backup circuit 365 drives the processor 334. A power supply system includes a Universal Serial Bus (USB) to serial converter 364 that couples a USB connector 363 to the processor 334. A battery/charge controller 362 allows the device 300 to be powered either through the USB connector 363 or by a rechargeable battery 361.

Processor 334 includes a memory 366 that stores parameters 367 for different manipulation exercise programs. The memory 366 also stores the resulting data 368 from the different manipulation exercises. For example, the processor 334 can measure the precise time and location of the rod 370 at an initial queue to thrust position and at a final primary thrust position. The programs, program parameters, and exercise result data can be transferred between the manipulation device 300 and a personal computer through the USB interface 363 and 364. The different stored exercise programs and associated parameters 367 can also be selected and the results viewed either through the user interface 340 or via the computer system coupled to USB connector 363.

For example, user accessible switch 337 can be used in conjunction with the user interface 340 to select a particular manipulation exercise where a thrust is measured from a neutral position where no pre-manipulative pressure is applied and a thrust is to be initiated into the device 300 without initially applying pressure to the device 300. Another type of manipulation exercise may require application of a pre-impulse pressure wherein enough pressure is applied to the device 300 to activate a timer in processor 334 and trigger a queuing signal that activates either a speaker 349 or light emitting diode 348 that indicates that enough pressure has been applied. A recoil style thrust can also be selected wherein a thrust may be initiated either from a neutral position or from a position of pre-impulse tension with the thrust being timed from the initial rod position to an ending rod position and back to the initial rod position, thereby adding the time it takes a therapist to recoil from the impulse end point into the total time of the thrust.

Switch 337 and user interface 340 can also be used to adjust the sensitivity of the device 30. For instance, greater sensitivity may be desirable for smaller patients whereas greater force is appropriate for larger patients. Similarly, different joints require different levels of force for manipulation. Therefore, different parameters for LOW, MEDIUM, HIGH and LARGE PATIENT exercises can be selected from the programs 367.

Switch 338 selectively activates and deactivates LED 348 and audio speaker 349. For example, selecting switch 338 may cause the processor 334 to generate a tone through speaker 349 and activate LED 348 when the reciprocating member 320 is thrust into a starting queue to thrust position. Deselecting switch 338 may cause the processor 334 to only activate LED 348 and disable any audio signal to speaker 349 during the manipulation exercise. Some of the different exercises that may selectively activate LED 348 and/or speaker 349 are described in more detail below.

Figure 6:
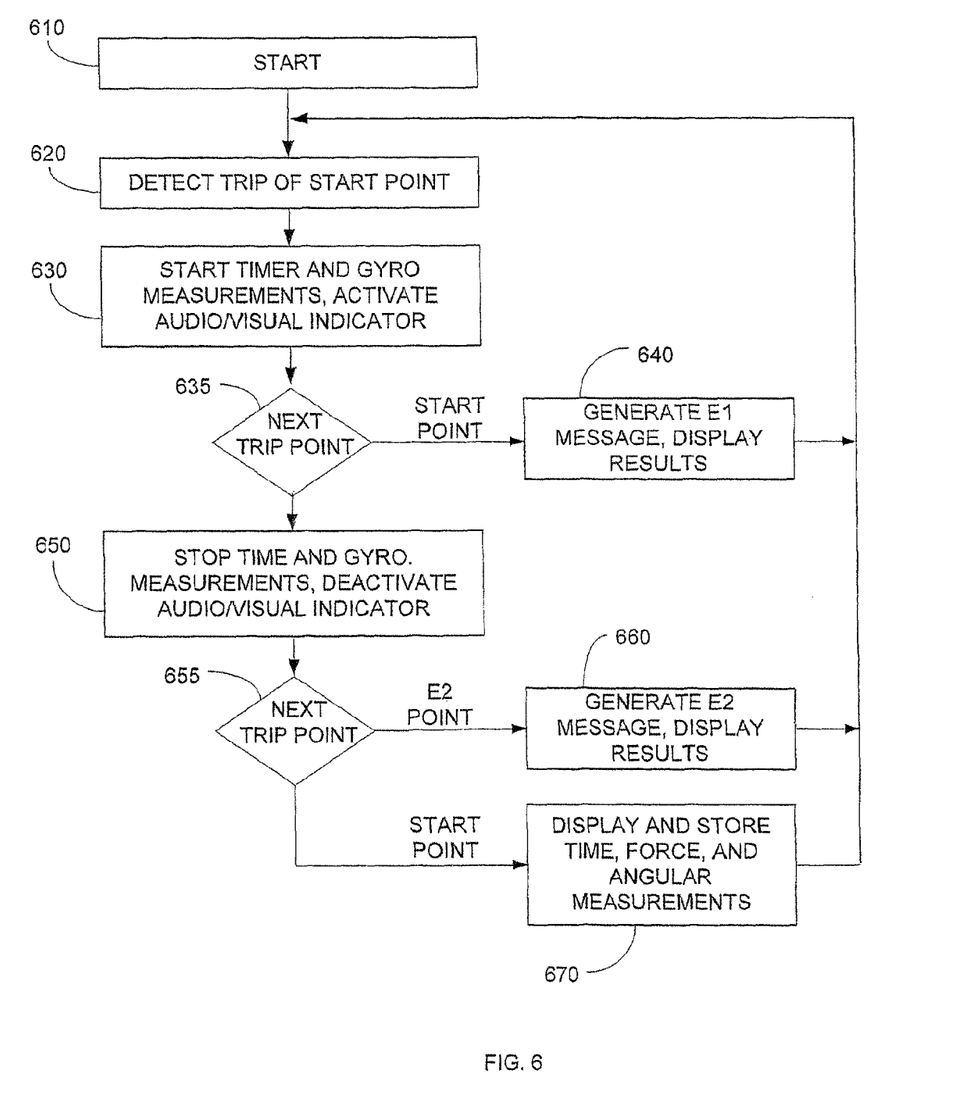
FIG. 6 is flow diagram showing how a programmable manipulation exercise is monitored by the control system in FIG. 5.

FIG. 6 is a flow diagram showing an example of a manipulation exercise that uses a START POINT, STOP POINT and E2 POINT where a standard impulse type is selected on user interface 340 in operation 610. Processor 334 checks the parameters settings associated with a particular selected program 367 (FIG. 5) to determine what parameters values to use for identifying the START POINT, STOP POINT and E2 POINT. For example, the START POINT may be 25 subunits past the first photo interrupter 332A (FIG. 5). The processor 334 in operation 620 waits for the user to press the reciprocating member 320 far enough into housing 350 so that the end 372 of rod 370 extends 25 subunits past photo interrupter 332A as indicated by the combination of signals from optical sensor 342 and photo interrupter 332A. During this first per-force stage, if photo interrupter 332B is also activated, the processor 334 determines that the user has pressed reciprocating member 320 too far into housing 350.

Upon reaching the START POINT as indicated by the sensors 332 and 342, the processor 334 in operation 630 selectively activates visual LED indicator 348 and/or audible speaker indicator 349 to indicate that pre-impulse pressure has been applied. The processor 334 then starts an internal timer and starts reading angular displacement and/or rotation measurements for gyroscope 344. Processor 334 monitors sensors 332 and 342 in operation 635 to determine which one of the START POINT and the STOP POINT next changes state. If the START POINT is reached next, then the pre-impulse pressure has been released and processor 334 outputs an E1 error message to the user interface 340, as indicated in operation 640. The error message may also include rod maximum position and angular displacement or rotation measurements. If the STOP POINT value is reached next by sensors 332 and 342, the processor 334 halts the visible or audio queuing tone 348 and/or 349, stops the gyroscope measurements, and stops the internal timer in operation 650.

Processor 334 in operation 655 determines which one of the E2 POINT and START POINT values is reached next. If the E2 POINT is actuated next, then the amplitude of the simulated impulse was too large and the rod 370 extended too far past the STOP POINT. The processor 334 outputs an E2 message to display 340 in operation 660 along with any position and angular data. On the other hand, if the START POINT is actuated next, then the correct amount of thrust was applied to the manipulation device. Accordingly, the end of rod 270 reached the STOP POINT and then receded back past the START POINT without ever reaching the E2 POINT. The processor 334 determines that a valid thrust was simulated and displays on interface 340 and stores in memory 360 the time measurement of the internal timer along with the position and angular information in operation 670.

The position information provided with an E1 error message identifies how close the reciprocating member 320 came to reaching the STOP POINT before falling back to the START point. The position information provided with an E2 error message identifies how far the rod 370 extended past the STOP point before falling back to the START point. In a successful exercise, the position information can indicate how far the rod 370 extended between the STOP POINT and E2 POINT before receding back past the START POINT. This position information is used in conjunction with the time information to determine an amount of force applied during the thrust. Precise force measurements can be derived because of the accurate position measurements provided by the combination of optical sensor 342 and photo interrupters 332. These precise force measurements allow a student to more accurately monitor progress in successfully executing different manipulation exercises.

The angular displacement information and/or angular rotation information derived by the processor 334 from gyroscope 344 indicates whether or not a substantially constant angle vector was maintained during the thrust and also indicates how much torque was applied during the thrust.

Figure 7:
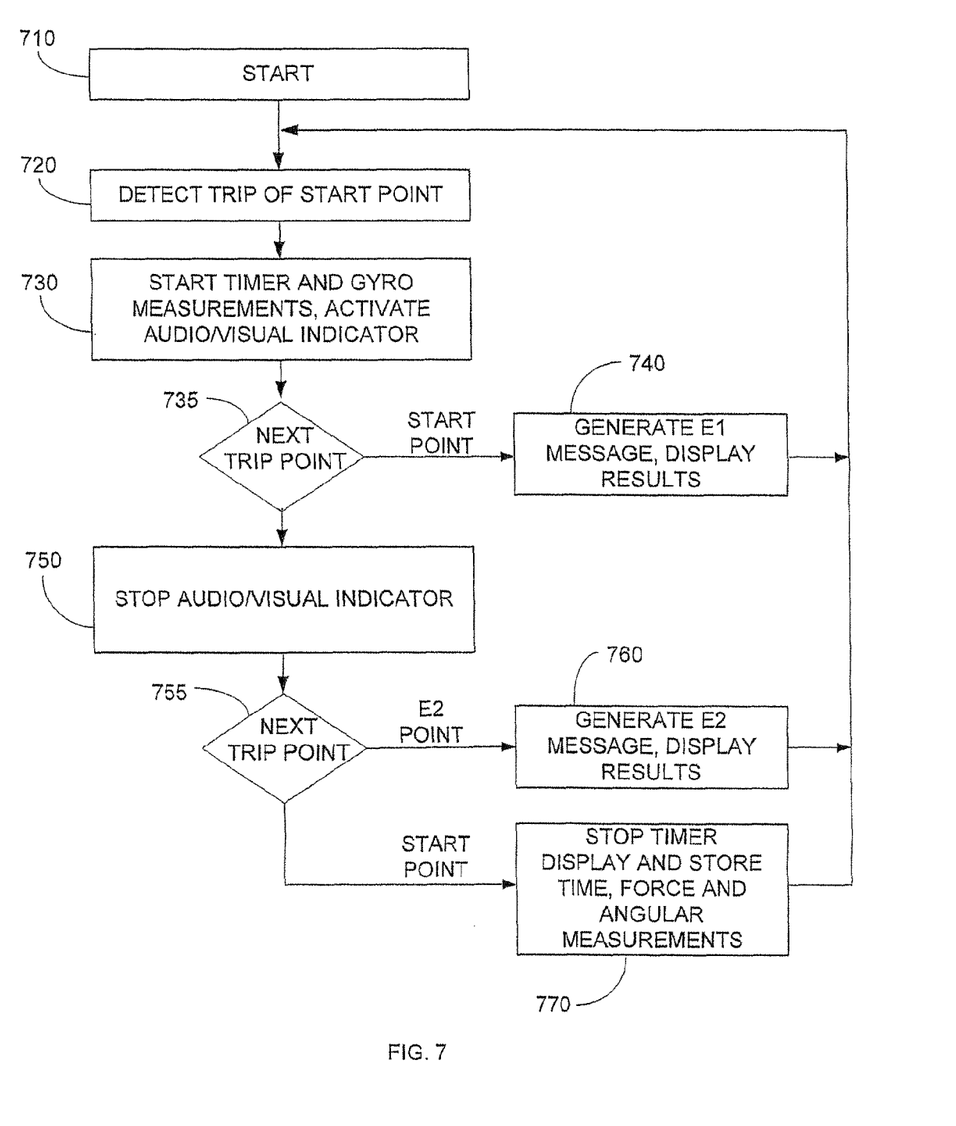
FIG. 7 is flow diagram explaining a second programmable manipulation exercise monitored by the control system in FIG. 5.

FIG. 7 is a flow diagram showing how the processor 334 operates when a recoil type manipulation exercise is selected from user interface 340. The operation in recoil mode is largely the same as the operation illustrated in FIG. 6. Processor 334 checks the particular type of manipulation exercise 367 selected via user interface 340 to determine which positions along axis 356 (FIG. 1) to use as the START POINT, STOP POINT and E2 POINT. The processor 334 then waits for the sensors 332 and 342 to indicate the end 372 of rod 370 has reached the START POINT in operation 720.

Upon the end of rod 370 reaching the START POINT, processor 334 generates the queuing tone via speaker 349 and/or queuing visual indicator via LED 348 to indicate that pre-impulse pressure has been applied. The processor 334 also starts the internal timer and gyroscope measurements. Processor 334 then monitors sensors 332 and 342 in operation 735 to determine which one of the START POINT and the STOP POINT is reached next by the end of rod 370. If the START POINT is reached next, then pre-impulse pressure has been released before reaching the desired STOP point. The processor 334 outputs the E1 error message to display 340 in operation 740.

As explained above, other information such as the maximum compression position or force information and angular displacement and rotation information can also be displayed and stored along with the error message. If the STOP POINT is reached next, then processor 334 halts the tone or visual indicator in operation 750, but not the internal timer. The processor 334 might stop recording the angular measurement information at this point, continue recording the angular measurement information, or record the maximum angular measurement value at the STOP POINT and then start recording a new angular measurement reading.

Processor 334 at step 755 monitors which one of the E2 POINT and START POINT is next reached by the rod 370. If the E2 POINT is next reached, the amplitude of the simulated impulse was too high and processor 334 outputs an E2 message to display 340 in operation 760. If the START POINT is next reached by the end of rod 370, a valid impulse was generated and processor 334 halts the internal timer and gyroscope measurements. The time, position/force, and angular measurements are then output to memory 360 and the display 340 in operation 770.

A LOW setting can be selected via user interface 340 to simulate low amplitude manipulations requiring a high degree of accuracy and which need only a standard level of pre-manipulative pressure, such as cervical spine manipulations. The LOW setting causes the processor 334 to use parameters associated with a lower START POINT and lower STOP POINT. For example, the START POINT and STOP POINT may be associated with relatively short distances of travel for rod 370 and the STOP POINT may be positioned relatively close to the E2 POINT. As a result, the manipulation exercise associated with the LOW setting may require a high degree of accuracy in order to reach the STOP POINT without also tripping the E2 POINT.

A MEDIUM setting approximates the thrust required for manipulations in the thoracic region of the spine which require higher amplitude levels and have a larger margin for error. The START POINT may remain at the same as the LOW setting since no greater level of pre-manipulative tension is needed. The STOP POINT, however, may be farther away from the STOP POINT in order to correspond to a higher amplitude level. Also, the E2 POINT may be moved to a location farther away from the STOP POINT in order to allow for a higher margin of error in amplitude level for the simulated impulse.

Similarly, a LARGE setting approximates the impulses required for manipulations in the lumbar region of the spine which require still higher amplitude levels and also have a large margin for error. The START POINT may remain at a same location since no greater level of pre-manipulative tension is needed. The STOP POINT, however, may move even farther from the START POINT in order to correspond to an even higher amplitude level. Also, the E2 POINT may be moved further away from the STOP POINT in order to allow for a higher margin of error in amplitude level for the simulated impulse.

A LARGE patient setting for a particular exercise 367 approximates the impulses required for high amplitude manipulations similar to the LARGE switch setting, but with a deeper level of pre-manipulative tension, as is typically required in manipulations performed on very large patients. The START POINT may move to a further location to simulate a greater level of pre-manipulative tension. The STOP POINT and E2 POINT may remain at the furthest position away from the START POINT. Other settings can be used for any programmable type of manipulation exercise.

Figures 8A, 8B, 8C:
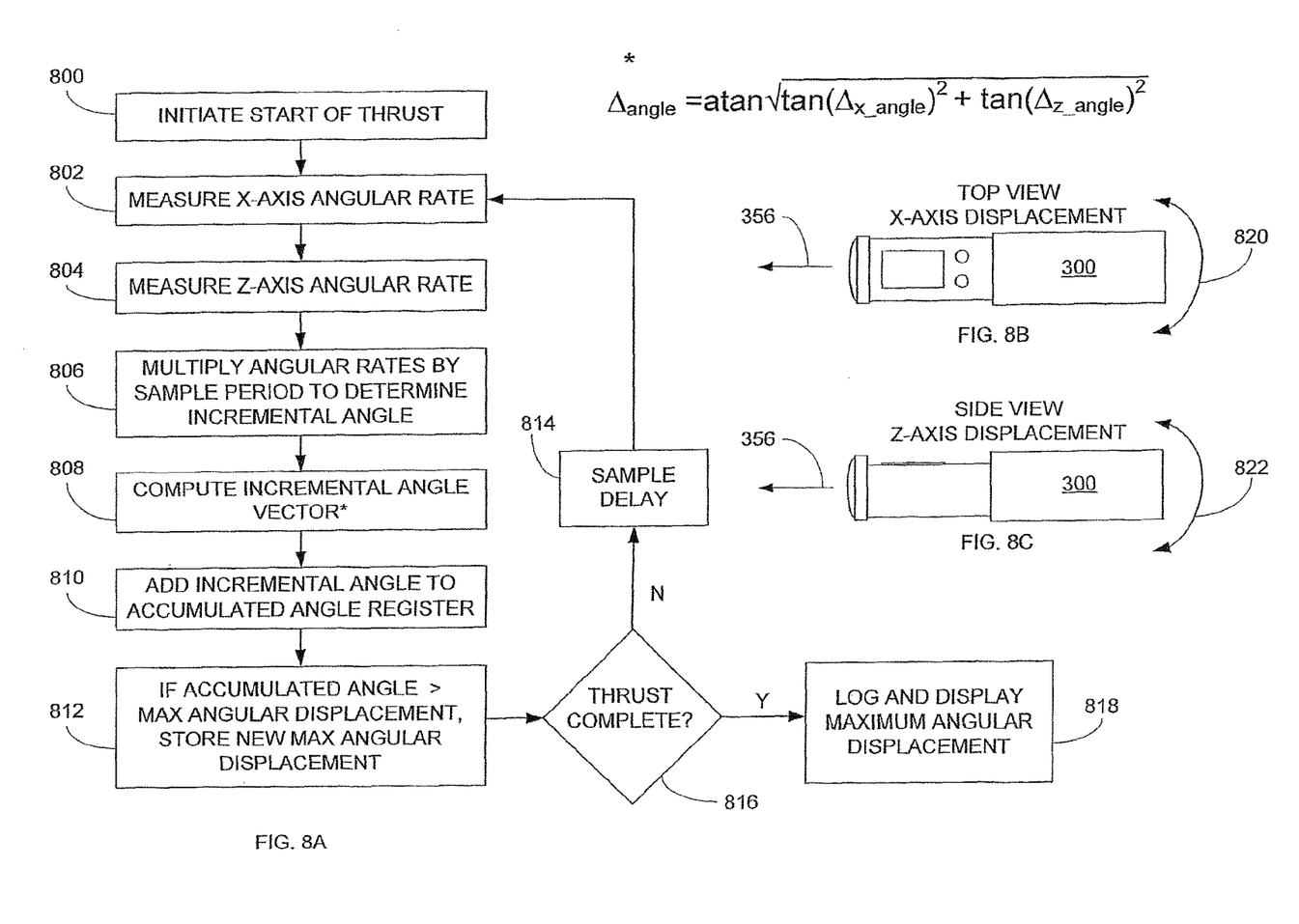
FIGS. 8A-8C show how the control system of FIG. 5 measures angular displacement during a manipulation exercise.

FIGS. 8A-8C show how the processor 334 calculates the angular displacement of the apparatus 300 during a manipulation exercise. In operation 800 a thrust is initiated by the user. For example, a user initiates a thrust at the queue to thrust START position described above. The processor 334 measures an X-axis angular rate in operation 802 and measures a Z-axis angular rate in operation 804 from the X and Y axis signals generated by the gyroscope 344 shown in FIG. 5. The X-axis displacement is shown in FIG. 8B and the Z-axis displacement is shown in FIG. 8C. In this example, the X-axis angular rate represents the rate of lateral/horizontal movement 820 of apparatus 300 relative to center line 356. The Z-axis angular rate represents the rate of vertical movement 822 of apparatus 300 relatively to center line 356.

The processor 334 multiplies the X and Z angular rates by a sample time period in operation 806 to determine an incremental X angle (X_angle) and an incremental Z angle (Z_angle). An incremental angle vector is computed according to the incremental X and Z angles by the processor 334 in operation 808 according to the following equation:

$$\Delta_{angle} = \mathrm{atan}\sqrt{\tan(\Delta_{x\_angle})^2 + \tan(\Delta_{z\_angle})^2}$$

The incremental angle is accumulated in a register with previously derived incremental angles derived over previous time delay periods in operation 810. If the accumulated angle value is greater than a previous derived maximum angular displacement in operation 812, then the new accumulated angle value is used as the new maximum displacement.

For example, the incremental angular displacement may be several degrees in a first sample time period but may move back toward zero degrees during a second sample time period. In this example, the new accumulated angle would be less than the previous accumulated angle and would not be greater than a previously derived maximum angular displacement. On the other hand, if the incremental angle vector continues to increase in a direction away from the center line 356 in next time period, the incremental angle vector could increase the accumulated angle increase beyond a prior previous maximum angular displacement value.

If the thrust has not completed in operation 816, then the processor 344 waits another sample delay period and calculates and accumulates another incremental angle vector in operations 802-812. When the thrust is completed in operation 816, the processor logs the maximum angular displacement value in memory 360 and also displays the angular displacement values on display 340 possibly along with any pass/fail, positional/thrust, and time information as described above in FIGS. 6 and 7.

Figures 9A, 9B:
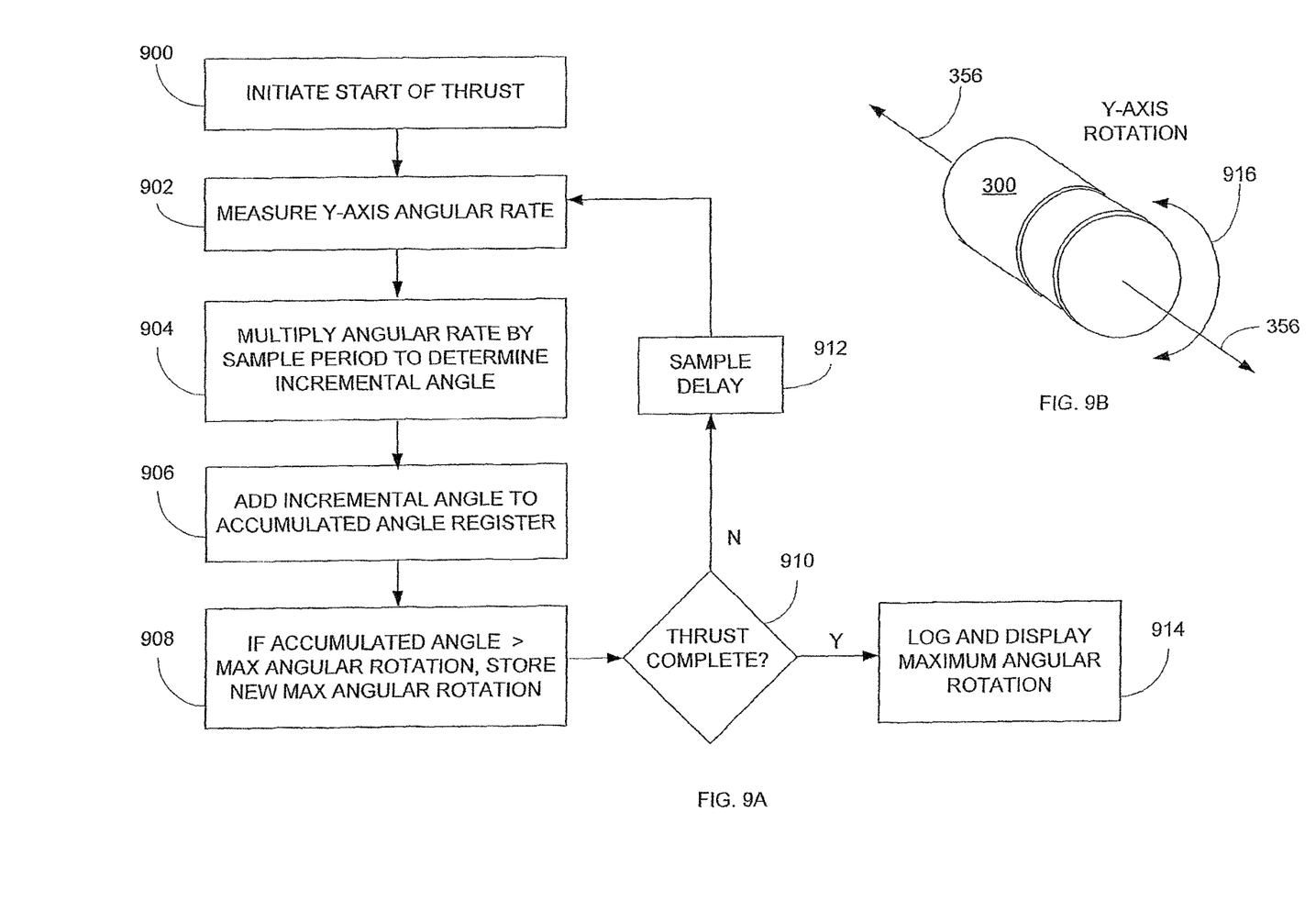
FIGS. 9A-9B show how the control system of FIG. 5 measures angular rotation during a manipulation exercise.

FIGS. 9A and 9B show how the processor 334 calculates the angular rotation or torque applied to the apparatus 300 during a manipulation exercise. In operation 900 a thrust is initiated by the user. The processor 334 measures a Y-axis angular rate in operation 902. The Y-axis displacement is shown in FIG. 9B. In this example, the Y-axis angular rate represents the rate of rotational movement 916 (torque) around center line 356 applied during the thrust to apparatus 300.

The Y angular rate is multiplied by the sample time period in operation 904 to determine an incremental Y angle. The incremental Y angle is accumulated in a register with previously derived incremental Y angles derived over previous time delay periods in operation 906. If the accumulated Y angle value is greater than a previous derived maximum angular rotation in operation 908, then the new accumulated angle rotation value is used as the new maximum angular rotation.

For example, the incremental angular rotation may be several degrees in a clockwise direction during a first sample time period but may rotate in an opposite counter clockwise direction during a second sample time period. In this example, the new accumulated angle would likely be less than the previous accumulated angular rotation and may not be greater than a previously derived maximum angular rotation.

One the other hand, if the incremental angle continues to rotate in a same clockwise direction around the center line 356 during a next sample time period, the incremental angle could increase the accumulated rotation beyond a previous maximum angular rotation value.

If the thrust has not completed in operation 910, then the processor 334 waits another sample delay period and calculates and accumulates another incremental angle in operations 902-908. When the thrust is completed in operation 910, the processor 334 logs the maximum angular rotation value in memory 360 and also displays the angular rotation value on display 340 possibly along with any pass/fail, positional/force, time, and angular displacement information as described above in FIGS. 6-8.

In the example shown in FIGS. 1 and 2, the patient 10 is in a prone position with the therapist 20 positioned above the patient with the thrust 30 is being applied posterior to anterior and slightly inferior to superior. The contact point on the patient 10 is in the mid-thoracic spine. This positioning is used to mobilize a thoracic spinal segment into flexion.

To simulate a manipulation, a particular manipulation exercise is selected on the user interface 340. In FIG. 2, the device 300 is then positioned by therapist 20 to thrust along the same vector 30 as the impulse of FIG. 1. The therapist then gently applies pressure to the end of the device 300 causing the elongate reciprocating body 320 to slide into elongate housing 350 (FIG. 3). The motion of elongate reciprocating body 320 with respect to elongate housing 350 is measured by the passage of the tip 372 of rod 370 past sensors 332 and 342.

The parameters associated with the particular selected exercise determine the START POINT which is then detected by the processor 334 from the sensors 332 and 342 (see FIGS. 6 and 7). If therapist 20 releases the pressure on device 300 after reaching the START POINT, the tip 372 of rod 370 will retreat back to the START POINT before reaching the STOP POINT. This causes the processor 334 to output the E1 message to display 340 indicating the loss of simulated pre-manipulative tension.

If, however, the simulated impulse is correctly delivered into device 300 and the STOP point is reached without losing the pre-manipulative tension, the internal clock is stopped by the processor 334. Should the therapist 20 force the tip 372 of rod 370 far enough to reach the E2 POINT, then the amplitude of the simulated impulse is too great and the processor sends the E2 message to the display 340. If the E2 POINT is not reached after reaching the STOP POINT, the internal timer continues to run until the tip 372 of rod 370 passes back past the START POINT. This halts the clock and causes the elapsed time to be displayed via display 340. This process can be repeated to simulate the manipulations for any region of the spine.

The processor 334 can also be programmed to detect fault conditions that determine in real-time if a thrust measurement is inaccurate due to a sensor fault. A fault condition is generated by the processor 334 when during a practice or regular thrust the optical sensor 342 (Sensor) indicates more than a +20% movement in the rod 370 (>pos1) but the tip of rod 370 is still not detected by the photo interrupter 332A. Another fault condition is generated when the optical sensor 342 identifies greater than 20% rod movement beyond photo interrupter 332A (>pos2) and photo interrupter 332B is still not activated. Another fault condition is generated when the optical sensor 342 identifies greater than 20% rod movement beyond photo interrupter 332B (>pos3) and photo interrupter 332C is still not activated. Another fault condition is generated when optical sensor 342 identifies greater than 20% rod movement beyond photo interrupter 332C (>pos4) and photo interrupter 332D is still not activated.

Another fault condition will be generated if the photo interrupter 332A activates and the optical sensor 342 still reads less than 20% movement of rod 370. Another fault condition will be generated if the photo interrupter 332B activates and the optical sensor 342 still reads less than 20% movement of rod 370 past photo interrupter 332A. Another fault condition will be generated if the photo interrupter 332C activates and the optical sensor 342 reads less than 20% movement of rod 370 past photo interrupter 332B. Another fault condition will be generated if the photo interrupter 332D activates and the optical sensor 342 still reads less than 20% of rod 370 past the photo interrupter 332C.

Other fault conditions detected by the processor 334 can include photo interrupter 332C activating without photo interrupter 332A first activating, photo interrupter 332C activating without photo interrupters 332A and 332B first activating, and photo interrupter 332D activating without photo interrupters 332A, 332B, and 332C first activating. Another fault condition may be generated when photo interrupters 332A, 332B, 332C, and 332D are all not deactivated at the start of a thrust.

During any detected fault condition, the processor 334 will cancel the thrust measurements and report a system fault by generating a fault message on the display 340 or generating an audio error buzzer tone through speaker 349.

Thus, the manipulation device 300 enables a therapist 20 to practice therapeutic manipulations and measure thrust times, thrust force and thrust angles at reduced risk of injury to either the therapist or a patient or training partner. The manipulation device 300 enables the therapist 20 to learn to produce high velocity impulses within a preselected amplitude and direction and develop strength and muscle coordination in specific muscle groups of the arms, hands and upper body to help produce high velocity repeatable thrusts.

Having described and illustrated the principles of the invention in an embodiment thereof, it should be apparent that the invention can be modified in arrangement and detail without departing from such principles. I/We claim all modifications and variations coming within the spirit and scope of the following claims.

The invention claimed is:

1. An apparatus comprising:
   a housing including an elongate body and an elongate reciprocating body adapted to fit into the cavity of the elongate body;
   a biasing member adapted to fit within the axial cavity of the elongate body and further adapted to bias the elongate reciprocating body to a first position relative to the axis of the cavity;
   a sensing device disposed in the elongate body comprising an image sensor and a plurality of photo interrupters, the image sensor configured to capture a plurality of images of the biasing member in response to movement of the biasing member about the axis of the cavity and each of the plurality of photo interrupters configured to generate a corresponding interrupter signal in response to movement of the biasing member about the axis of the cavity; and
   a processor configured to quantify a therapeutic manipulation force applied during therapeutic manipulation based on the plurality of images and on the interrupter signals.

2. The apparatus according to claim 1 wherein the sensing device further comprises a gyroscope configured to generate an X-axis signal that identifies a rate of angular displacement along an X-axis of the housing.

3. The apparatus according to claim 2 wherein the sensing device is configured to generate a Z-axis signal that identifies a rate of angular displacement along a Z-axis of the housing.

4. The apparatus according to claim 3 wherein the processor determines an angular displacement rate of the apparatus during application of the therapeutic manipulation force according to both the X-axis signal and the Z-axis signal.

5. The apparatus according to claim 3 wherein the processor is configured to multiply the angular displacement rate by a predetermined time period to identify an incremental displacement angle and determine a maximum displacement of the housing during the therapeutic manipulation force by accumulating incremental displacement angles derived for previous time periods.

6. The apparatus according to claim 2 wherein the sensing device is configured to generate a Z-axis signal that identifies a rate of Y-axis angular displacement of the housing.

7. The apparatus according to claim 6 wherein the processor determines an amount of torque applied to the apparatus during application of the therapeutic manipulation force according to the Y-axis signal.

\* \* \* \* \*